(12) United States Patent
Reymond et al.

(10) Patent No.: US 8,092,445 B2
(45) Date of Patent: Jan. 10, 2012

(54) FLUID CONNECTION DEVICE, SYSTEM AND METHOD FOR CONTINUOUSLY TAKING FLUID MICROSAMPLES USING THIS DEVICE

(75) Inventors: Jean-Marc Reymond, Saint-Remy-les-Chevreuse (FR); Sophie Kerhoas-Cavata, Raizeux (FR); Philippe Mangeot, Le Kremlin-Bicetre (FR); Raphael Boisgard, Nozay (FR)

(73) Assignee: Commissariat a l'Energie Atomique, Paris (FR)

( * ) Notice: Subject to any disclaimer, the term of this patent is extended or adjusted under 35 U.S.C. 154(b) by 851 days.

(21) Appl. No.: 11/954,994

(22) Filed: Dec. 12, 2007

(65) Prior Publication Data

US 2008/0319344 A1    Dec. 25, 2008

(30) Foreign Application Priority Data

Jun. 19, 2007   (FR) ..................................... 07 04349

(51) Int. Cl.
*A61M 25/16* (2006.01)
(52) U.S. Cl. ........................ 604/533; 600/573
(58) Field of Classification Search .......... 600/574–579, 600/585; 604/240, 523, 181, 533
See application file for complete search history.

(56) References Cited

U.S. PATENT DOCUMENTS

| | | | | |
|---|---|---|---|---|
| 4,254,773 A | * | 3/1981 | Waldbillig | 604/534 |
| 4,559,043 A | * | 12/1985 | Whitehouse et al. | 604/201 |
| 4,834,719 A | * | 5/1989 | Arenas | 604/243 |
| 4,981,469 A | * | 1/1991 | Whitehouse et al. | 604/86 |
| 5,286,067 A | * | 2/1994 | Choksi | 285/38 |
| 5,312,377 A | * | 5/1994 | Dalton | 604/534 |
| 5,456,676 A | | 10/1995 | Nelson et al. | |
| 6,165,149 A | * | 12/2000 | Utterberg et al. | 604/5.01 |
| 6,595,964 B2 | * | 7/2003 | Finley et al. | 604/246 |

FOREIGN PATENT DOCUMENTS

| | | |
|---|---|---|
| EP | 0 688 993 | 12/1995 |
| FR | 2 395 037 | 1/1979 |
| WO | WO 02/43589 | 6/2002 |

OTHER PUBLICATIONS

ISO 594-2, International Standard, Second Edition Sep. 1, 1998, Conical Fittings with 6% (Luer) taper for syringes, needles and certain other medical equipment—Part 2: Lock Fittings.*
Search Report from priority document French Patent No. 07/04349, filed Jun. 19, 2007.

* cited by examiner

*Primary Examiner* — Nicholas D Lucchesi
*Assistant Examiner* — Melissa A Snyder
(74) *Attorney, Agent, or Firm* — Alston & Bird LLP

(57) ABSTRACT

The invention relates to a fluid connection device and to a continuous automated system and method for taking fluid microsamples using this device.
A device (20) according to the invention, which is intended to be connected to a first line (21) via a first opening and includes a second opening through which a second line (28) passes, comprises:
  a female fluid connector (22) that defines the first opening and has an internal fitting surface (23) terminating in a female end (24) into which this first line opens; and
  a male fluid connector (25) that defines the second opening, which is fitted into the female connector via its external surface (26) and terminates via its male radial end (27) inside the female connector.
According to the invention, this second line is formed from a flexible microtube pushed right through the male connector beyond the male end, the free end of the second line pressing in a sealed manner against the female end so as to minimize the dead volume between the first line and the male connector.

8 Claims, 3 Drawing Sheets

FLUID CONNECTION DEVICE, SYSTEM AND METHOD FOR CONTINUOUSLY TAKING FLUID MICROSAMPLES USING THIS DEVICE

FIELD AND BACKGROUND OF THE INVENTION

The present invention relates to a fluid connection device with no dead volume, which is intended for transferring a fluid, and also to an automated system and method for continuously taking a series of liquid microsamples in such a way that the samples thus taken are in discrete packets in space and in time as far as their temporary storage container, for subsequent treatment. The invention applies more particularly, but not exclusively, to a fluid connection device for transferring whole blood microsamples from a mammal, for example a rat or a mouse.

The fluid connection devices that are used both in medicine and biology in relation with a catheter or the like, on the one hand, and with a flexible microtube, on the other hand, are usually standardized connectors of the "Luer" type defined by the ISO 594-1 standard of 1986 or else of the "Luer-lock" type defined by the ISO 594-2 standard of 1998. Referring to FIG. 2 appended to the present description, the usual connection devices 20' essentially comprise:

- a female fluid connector 22' into which a catheter is pressed, said connector having a conical internal fitting surface 23' that converges on a female end 24' into which this catheter opens; and
- a male fluid connector 25' which is fitted into the female connector 22' via its conical external surface 26' which has the same conicity as the internal surface 23' of the female connector and converges on a male end 27' leaving, in the state of maximal insertion, a distance dl from the female end 24' (see FIG. 2).

Table 1 below lists the main dimensional characteristics of Luer connection devices (6% conicity angle) depending on the material used, according to the aforementioned standard.

TABLE 1

| Dimensional parameter | | Description | Dimensions (mm) Rigid material | Semirigid material |
|---|---|---|---|---|
| Base dimensions | $d_{min}$ | Minimum diameter of the end of the male conical connector (reference diameter) | 3.925 | 3.925 |
| | $d_{max}$ | Maximum diameter of the end of the male conical connector | 3.990 | 4.027 |
| | $D_{min}$ | Minimum diameter of the opening of the female conical connector | 4.270 | 4.270 |
| | $D_{max}$ | Maximum diameter of the opening of the female conical connector | 4.315 | 4.315 |
| | E | Minimum length of the male conical connector | 7.500 | 7.500 |
| | F | Minimum depth of the female conical connector | 7.500 | 7.500 |
| Other dimensions | L* | Minimum penetration | 4.665 | 4.050 |
| | M* | Variance over the penetration of the | 0.750 | 0.750 |
| | N* | female connector Variance over the penetration of the male connector | 1.083 | 1.700 |
| | $R^{**}{}_{max}$ | Radius of curvature | 0.5 | 0.5 |

With reference to the symbols * and ** of this table:
*the dimensions L, M, N result from the base dimensions; and
**or equivalent entry chamfer not having sharp angles.

A major drawback of the connection devices defined by the aforementioned standards is that the distance dl (typically about 3 mm) between the respective ends of the male and female connectors generates an intrinsic dead volume that becomes detrimental in various circumstances. The most frequent occurs when the connectors are used for circulating very small liquid samples, of the order of magnitude comparable to or even smaller than this dead volume. To give an example, when injecting or taking mammal blood microsamples, it is general practice to use a flexible line provided with a connector having a diameter of about 4 mm, the space thus delimited determining a dead volume of around 15 µl to 30 µl, which may cause the following problems in use:

- since several successive microsamples serve to fill said dead volume, this delays the passage of the first microsamples and means that a larger volume of fluid is taken, which is lost; and
- since the cross section of the fluid line is considerably enlarged owing to this dead volume, various microsamples become mixed up with one another, which is detrimental if the fluid is a liquid, and these microsamples are used subsequently, for example for the purpose of analysis. This impairs their traceability and is particularly prejudicial in the case of monitoring rapid biological phenomena during which it is of fundamental importance for each microsample to be able to retain its initial characteristics over the entire length of the distribution line.

Other drawbacks may also result therefrom, such as a need to purge the line if it is desired to avoid any mixing with a residual fluid, this purging operation being moreover particularly difficult to carry out owing to the existence and the shape of the dead volume.

Known elsewhere, from the document U.S. Pat. No. 4,966,588, is the use, for injecting a therapeutic liquid substance, of a fluid connection device essentially comprising:

- a male connector fitted into a female connector via respective cylindrical fitting surfaces provided with shoulders, this female connector being intended to receive a cannula forming an injection tip; and
- a rigid injection needle that is inserted so as to pass through both the male connector and the female connector and also the cannula, by piercing a sealing washer positioned between the two connectors, and which is intended to be implanted into the body to be treated.

A major drawback of this device employing a rigid injection needle that passes right through the connectors and the cannula lies in the small diameter of this needle compared with that of the opening of the male connector. Another drawback arises from the fact that the sealing washer may be unintentionally displaced following removal of the needle from the connectors after injection. This may cause positioning problems in the case of multiple use, or else may mean that the sealing washer, which is difficult to access, has to be changed at each use.

Finally, another drawback lies in the fact that the needle that perforates the sealing washer necessarily has a certain length, which may become problematic upstream or downstream of the needle. Thus, it is not at all suitable for injecting a liquid or for removing blood samples in a small mammal, such as a rat or mouse. In particular in rats, it is general practice to use the caudal vein of the animal (or, for injection, the caudal artery) by introducing a catheter directly connected to the flexible line via a connector. Introducing a metal needle of a certain length through the sealing washer assumes that this needle protrudes into the vein (or the artery), which can then be damaged when the animal moves its tail.

SUMMARY OF THE INVENTION

One object of the present invention is to propose a fluid connection device which is intended for transferring a fluid, such as microsamples to be taken (in this first case, for example blood) or to be injected (in this second case, in general a liquid), and which is intended to be connected to a first line via a first opening in this device, which includes a second opening through which a second line passes, the second line being intended to communicate with the first line in order to transfer this fluid, the device comprising:

a female fluid connector that defines said first opening into which said first line is intended to be inserted and has an internal fitting surface terminating in a female radial end into which this first line opens; and a male fluid connector that defines said second opening, which is fitted into the female connector via its external surface and terminates via a male radial end inside the female connector, which device remedies all the aforementioned drawbacks.

For this purpose, a device according to the invention is such that this second line is formed from a flexible microtube which is pushed right through the male connector axially beyond said male end, the free end of this second line pressing in a sealed manner against said female end so as to minimize the dead volume between the first line and the male connector.

The term "microsamples" is understood within the present description to mean liquid samples, such as blood samples, each having a volume with less than 100 µl and preferably 30 µl or less (i.e. typically samples taken from small animals). Preferably, each microsample according to the invention is a total blood sample from a mammal of the rat or mouse type and has a volume ranging from 8 µl to 30 µl.

It should be noted that this dead volume minimized by the device according to the invention makes it possible to remedy the aforementioned drawbacks associated with the flow of microsamples, typically having volumes of 30 µl or less, with the known connection devices (delayed passage of the first microsamples, loss of liquid volumes taken and mixing of the microsamples impairing their traceability, in particular).

According to another feature of the invention, said internal fitting surface of the female connector may be a conical surface converging on said female end with the same conicity as said external surface of the male connector, which converges on said male end. Preferably, said male and female connectors may both be connectors of the "Luer" type, as defined by the ISO 594-1 standard of 1986, or else of the "Luer-lock" type, as defined by the ISO 594-2 standard of 1998.

Preferably, said second line may extend beyond said male end by an axial length at least equal to the minimum distance dl separating said respective ends of the two connectors when the male connector is pushed right into the connection position in the female connector in accordance with one or other of said standards.

Also preferably, said second line is provided, around its cylindrical wall and near its free end, with a stiffening means capable of stiffening it inside said female connector.

Advantageously, said stiffening means is formed from a ring made of a material that has a stiffness at least equal and preferably greater than that of said second line and is capable of being fastened thereto, it being possible for this fastening to be direct or via said male fluid connector. In the latter case, the male fluid connector is necessarily fastened to said second line.

According to a preferred variant, the stiffening means is fastened to the end of the second line, which it clamps, and is mounted so as to bear between the latter and said conical internal fitting surface of the female connector. As an example, this stiffening means may be based on a polymeric resin.

This ring may be attached around the second line or else coextruded with the latter. According to a variant more suitable for industrial production, the male connector may be produced in a single molding operation, after a slight remachining of the initial shape of the mold allowing the incorporation of this stiffening means.

As regards said first line with which the connection device according to the invention is equipped, this is advantageously a flexible microtube suitable for taking said liquid from an animal or injecting it thereinto, such as a flexible catheter to be implanted into the caudal vein of a small mammal for the purpose of taking blood microsamples.

An automated sampling system according to the invention for continuously taking a series of liquid microsamples from a body containing a liquid to be taken, such as blood microsamples from a mammal of the rat or mouse type, the system comprising a succession of lines that are joined together by a metering pump, such as a peristaltic pump, for sucking up, in bursts, a defined amount of the liquid to be conveyed to a storage container, this succession of lines including a first flexible line of the catheter type, which is intended to be implanted into this body and is connected to a connection device for transferring the microsamples toward the pump, is characterized in that this connection device is as defined above (i.e. including said second line extending this first line).

According to another feature of the invention, said sampling system is linked to a computer-aided control device which is in particular provided for controlling said pump.

According to another feature of the invention, said succession of lines has an approximately constant cross section, so that the microsamples following one after another each flow over an axial length that is greater than at least five times the largest internal transverse dimension of these lines (e.g. their internal diameter).

If the invention is intended to produce a discontinuous succession of samples for the purpose of supplying a downstream device, the succession of lines may advantageously terminate in a more rigid portion acting as micronozzle. In this case, to make it easier to deposit the microsample, the end of the micronozzle comes into contact with the receiving wall of said downstream device, this wall preferably making an angle of between 5° and 85° with the plane of section of the end of said micronozzle. Preferably, this angle is approximately equal to 45°. This is because if this angle is greater than 90°, then all or part of this drop formed by the micronozzle would remain attached thereto for surface tension reasons.

According to another essential feature of the invention, the enlargements in cross section of said succession of lines are all 20% or less in terms of area ratios, in such a way that the microsamples following one another in these lines are in discrete packets in space and in time, in particular so that those with a volume of 30 µl or less are practically never mixed together therein.

According to another feature of the invention, said flexible microtube forming said second line is extended by at least one portion, at least particularly flattened and of oblong cross section, which is designed to minimize the attenuation of particles emitted by each liquid microsample flowing in this portion so as to optimize the counting of these particles, such as electrons or positrons resulting from beta minus or beta plus decay, or else photons for example in the case of counting by fluorescence.

Preferably, said flattened portion has an approximately rectangular cross section, the long sides and/or the short sides of which are curved with mutually symmetrical curvatures, so that this portion has at least in part an approximately convex or concave external face.

Advantageously, said flattened portion has an [internal height (h)/internal width (l)] ratio of less than 20% and preferably between 5% and 10%, in which the internal height and internal width represent the smallest and largest transverse dimensions, respectively, of this portion, measured along two approximately perpendicular directions.

Also advantageously, the area ratio of the flow cross section of said flattened portion to that of each cylindrical portion adjacent this flattened portion may be equal to 35% or less.

Preferably, said internal height of the flattened portion may be less than 500 µm and preferably between 100 µm and 200 µm, the or each adjacent cylindrical portion possibly having a diameter of the order of 1 mm.

According to another feature of the invention, said flattened portion advantageously has a wall thickness e (expressed in µm) and a density d (expressed in $g/cm^3$), the product e×d of which is less than 100 and preferably less than 50, in such a way that the attenuation by this portion of the particles to be counted is minimized when the particles are electrons or positrons (the attenuation in both these cases being, as is known, proportional to this product e×d).

Advantageously, said flattened portion is based on a polyimide, for example "Kapton", having a density of between 1.3 and 1.5 $g/cm^3$ and this flattened portion has a wall thickness of less than 50 µm and preferably less than 30 µm. This flattened portion is for example obtained by thermoforming.

According to another feature of the invention, said flattened portion is equipped, facing its large faces and extending beyond its small faces, with two sets of detectors capable of counting said particles of each liquid microsample flowing therein.

It should be noted that this overhang of the detectors makes it possible to optimize the "capture" of the particles to be counted (geometric acceptance notion).

Advantageously, said detectors are placed against or in the immediate vicinity of said large faces.

According to another feature of the invention, the microsamples taken are of the whole blood of a mammal, comprising a plasma and globules, and said system may include, upstream of said computer-controlled metering pump:

a device for counting α, β or γ radioactivity (α or γ particles and electrons or positrons) highly attenuated by the materials through which it passes, emitted by a radiotracer diluted in this whole blood, this counting device also being computer-controlled and comprising, inside the measurement box said sets of detectors, such as silicon diodes, which are distributed substantially against said two plates, and also an electronic processing/interfacing card for these measurements; and an electronic module for detector read-out and data acquisition and transfer.

It should be noted that this system may thus advantageously carry out these measurements immediately after the microsamples have been taken.

An automated method according to the invention for continuously taking liquid microsamples from a body containing the liquid to be taken, such as blood microsamples from a mammal of the rat or mouse type, is noteworthy in that these microsamples are taken continuously, by an automated sampling system as defined above, according to a monotonic time function by the sending, to this sampling system and at preprogrammed instants $t_i$, by a computer-aided control device, signals for taking a microsample of preprogrammed volume, so that these microsamples thus taken via the metering pump follow on spatially and temporally along said succession of lines as far as said storage container.

Advantageously, it should be noted that the minimum sampling time is one second with the continuous sampling method according to the invention, which represents half the sampling time used in the prior art.

Thus, the sampling system according to the invention makes it possible in particular to carry out and link together, automatically (i.e. without any manual intervention), a sequence of two functions, both being automated, which consists, on the one hand, of the taking of microsamples—preferably blood microsamples—which are temporally and spatially in discrete packets (readily separable, for example via a break in the microtube) and, on the other hand, for example of a spatial separation in each microsample of at least one of its phases in order to subject it to a differentiated action, especially for the purpose of measuring the input function for nuclear imaging on small mammals, in particular for quantitative imaging of tracers in PET (positron emission tomography).

It should be noted that the small size of the animals that are preferably used for taking the microsamples requires the total volume of these microsamples to be limited to an amount that is compatible not only with the health of the animal but also with as small as possible a disturbance of its metabolism.

BRIEF DESCRIPTION OF THE DRAWINGS

The above features of the present invention, together with others, will be more clearly understood on reading the following description of several exemplary embodiments of the invention, given by way of nonlimiting illustration, said description referring to the appended drawings in which.

DETAILED DESCRIPTION

Figure 1:
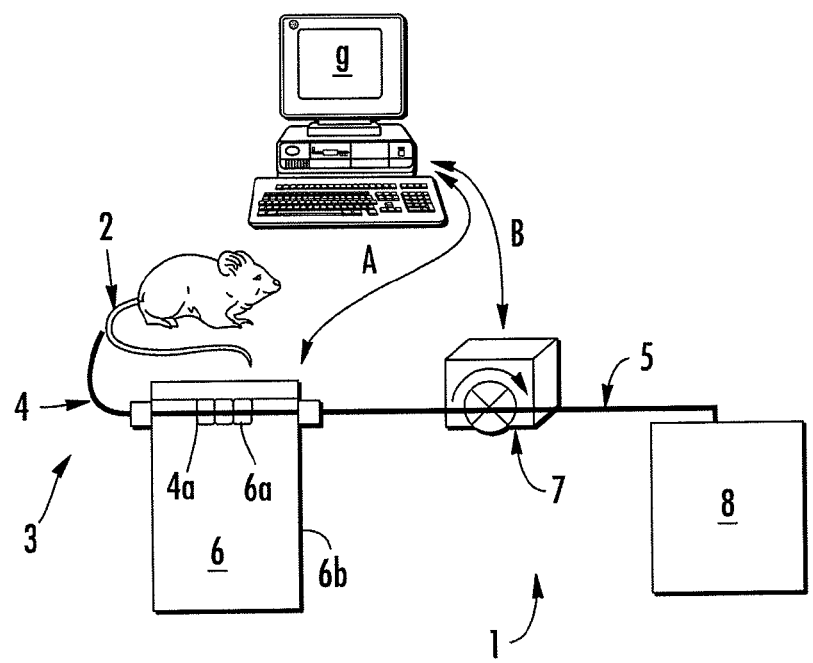
FIG. 1 is a schematic partial view of an automated sampling system according to the invention, including a measurement system such as a counter for counting the particles emitted by the beta radioactivity, placed upstream of a sample treatment device for treatment of the microsamples taken.

FIG. 1 illustrates by way of example a continuous automated installation 1 for carrying out, in succession and continuously, the taking of blood microsamples from a small mammal 2, for example of the rat or mouse type, for temporarily storing said microsamples and for carrying out measurements thereon, by means of a sampling system 3 that includes a succession of lines 4 and 5 of the flexible capillary or microtube type. This sampling system 3 essentially comprises:

- a catheter 21 which is equipped with a connection device 20 (both being visible in FIG. 3) and is intended for sucking out, in bursts, the same amount of blood to be taken, via a peristaltic pump 7;
- a counting system 6 for counting the particles present in the microsamples taken, which in this example is one that counts the particles resulting from the beta radioactivity 6 in the case of whole blood microsamples and which is placed as close as possible to the sampling point, being virtually in contact with a measurement portion 4a of this succession of lines 4, 5 (as explained below, this portion 4a has shape and material characteristics that are optimized for this counting and is centered with respect to the detection diodes 6a that the counter 6 comprises);
- a sample treatment system 8 placed downstream of the peristaltic pump 7, where these microsamples taken and analyzed are stored and treated; and
- a computer-aided control device 9 for controlling the entire system 3, including this pump 7 (see the double arrows A and B in FIG. 1 for this control).

According to the invention, the succession of lines 4 and 5 is such that the enlargements in their cross section present along these lines are always less than or equal to 20% in terms of area ratios so that the microsamples following one another in this succession of lines 4 and 5 undergo practically no mixing therein by diffusion. In this way, these microsamples are in discrete packets spatially and temporally.

Figure 3:
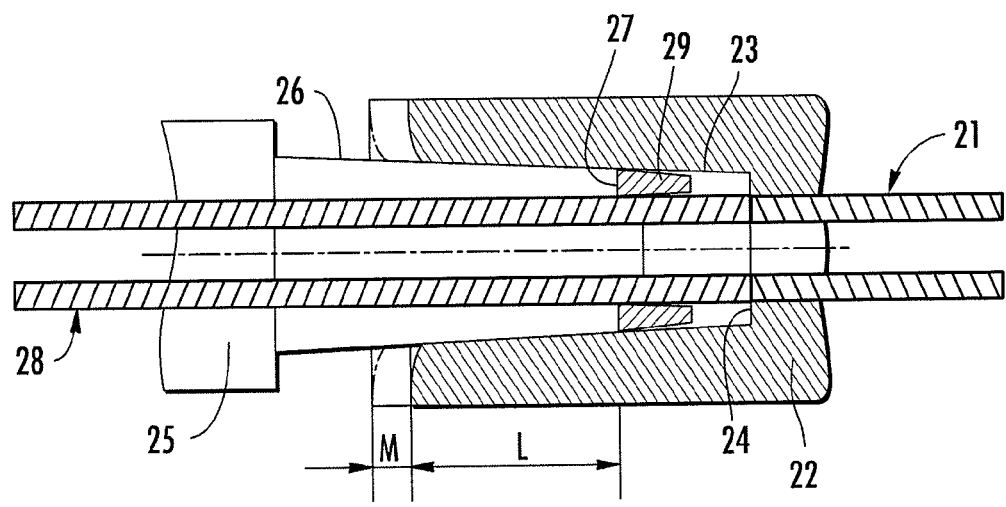
FIG. 3 is a partial view in radial section of a connection device with male and female connectors according to the invention, which is intended to be connected to this catheter and which forms an upstream part of the sampling system of FIG. 1.

As illustrated in FIG. 3, the connection device 20 according to the invention comprises, connected to the flexible catheter 21 intended to be implanted for example into the caudal vein of the mammal 2 and having for example an outside diameter of 1.5 mm and an inside diameter of 0.8 mm:

- a female fluid connector 22 into which the catheter 21 is pushed, said connector having a conical internal fitting surface 23 converging on a female radial end 24 into which the catheter 21 opens;
- a male fluid connector 25 which is fitted into the female connector 22 via its conical external surface 26 having the same conicity as this internal surface 23 of the female connector 22 and which converges on a male radial end 27; and
- a flexible microtube 28 made of LDPE (low-density polyethylene, such as an "LDPE 50" or an "LDPE 100") suitable for conveying the microsamples taken into a storage container, said microsamples being in discrete packets in space and in time, said microtube being pushed right into the male connector 25 axially beyond the male end 27 and so as to be immediately adjacent to the facing female end 24 so as to minimize the localized dead volume inside the female connector 22 between these two respective ends 27 and 24.

More precisely, these connectors 22 and 25 are Luer connectors as defined by the ISO 594-1 standard of 1986 or Luer-lock connectors as defined by the ISO 594-2 standard of 1998.

Preferably, the microtube 28 passes beyond the male end 27 by an axial length that is at least equal to the minimum distance dl separating the ends 27 and 24 when the male connector 25 is pushed into the connection position in the female connector 22 in accordance with one or other of these standards. In fact, and as illustrated in FIG. 3, this microtube 28 bears in a sealed manner against the female end 24.

Figure 2:
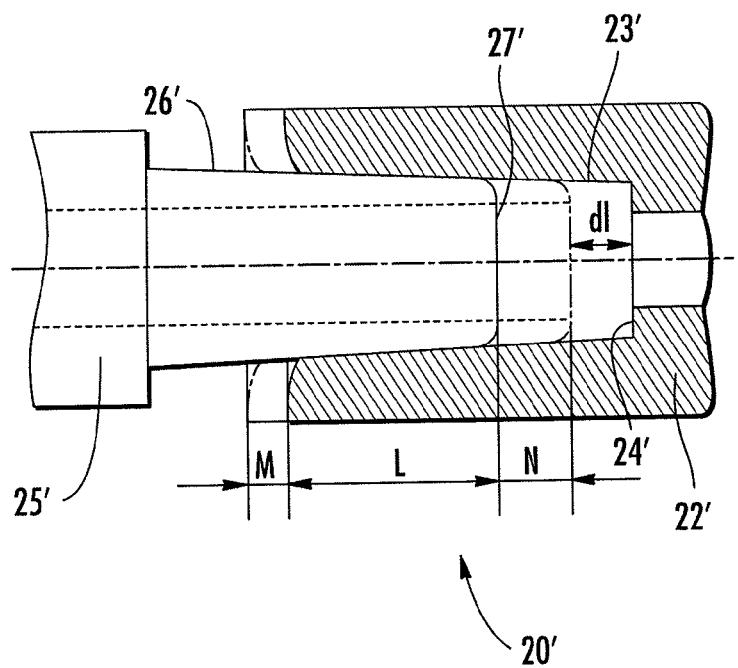
FIG. 2 is a partial view in radial section of a connection device with male and female connectors of known type, which is intended to be connected, on one side, to a catheter and, on the other side, to a flexible microtube for taking the microsamples.

The male connector 25 according to the invention makes it possible to overcome the dead volume inherent in the aforementioned length difference dl when referring to the known connection devices illustrated in FIG. 2.

As illustrated in this FIG. 3, the microtube 28 of the invention is provided, at its free end adjacent to the catheter 21, with a stiffening ring 29 mounted between the cylindrical wall of the microtube 28 and the internal surface 23 of the female connector 22. Advantageously, the stiffening means 29 is formed by a ring made of a material having a stiffness at least equal to and preferably greater than that of the microtube 28 and capable of being fastened thereto, it being possible for this fastening to be direct or via the male connector 25. In the latter case, the male connector 25 is necessarily fastened to the microtube 28.

According to a preferred variant, the ring 29 is fastened to the end of the microtube 28 and may be based on a polymeric resin. This ring 28 may be attached around the microtube 28 or else coextruded with the latter.

The connection device 20 according to the invention is produced from a device 20' of the prior art by drilling an orifice of annular cross section therein, so as to forcibly introduce the microtube 28 thereinto (the sharp cut at the end being perpendicular to the axis of the microtube 28).

It should be noted that the male connector 25 according to the invention is thus compatible with the entire range of standard female Luer devices according to the aforementioned standards and advantageously makes it possible to eliminate the dead volume in the connection device 20 (this dead volume possibly corresponding to a 20% increase in cross section relative to the minimum cross section of the line) and, consequently, to transfer, particularly blood microsamples, without any risk of them becoming mixed (and therefore with perfect traceability, the samples leaving the line being in accordance with those entering the line). Furthermore, this arrangement avoids having to wait for an excessively large number of microsamples to be taken in order to start the measurements or analyses, and also prevents a liquid volume corresponding to the dead volume being wasted.

Figure 4:
FIG. 4 is a photograph illustrating the shape and relative dimensions, in comparison with a euro 10 cent piece, of a line of the sampling system according to the invention provided downstream of this connection device and having a flattened portion for the particle counting carried out by the measurement system of FIG. 1.
Figure 4A:
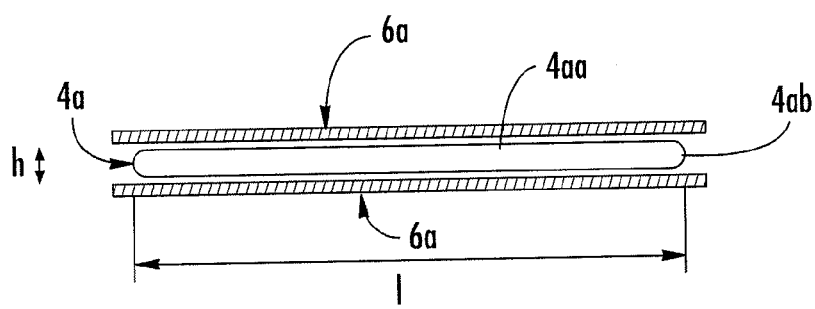
FIG. 4a is a schematic view in cross section of this flattened portion according to the invention, equipped with two sets of detectors illustrated in FIG. 1.

As illustrated in FIGS. 4 and 4a, a flattened measurement portion 4a is provided in the succession of sampling lines according to the invention, which flattened portion extends said second line 28 of FIG. 3 and is designed to optimize the counting by the particle counting system 6 of FIG. 1 (such as the beta counter, advantageously used for measuring the entry function of the small mammal 2). In this way the detection volume chosen is reduced and the counting efficiency is increased.

For this purpose, said flattened measurement portion 4a of oblong cross section is produced by thermoforming and is made of a polyimide of the "Kapton" brand (having a density of 1.42 g/cm$^3$ and a wall thickness of 25 μm±10%), which portion links together two cylindrical lines, for example made of LDPE, having an internal diameter for example of about 1 mm. As illustrated in FIG. 4a, the aforementioned detection diodes 6a of the counting system 6 are arranged on either side of this portion 4a relative to its smallest transverse dimension, consisting here of its height h.

In this exemplary embodiment, the flattened portion 4a has an approximately rectangular cross section, the short sides of which are curved with mutually symmetrical convex curvatures, and this portion has an [internal height h/internal width l] ratio of about 8%, where the internal height and the internal width are equal to 130 μm and 1490 μm respectively.

As regards the area ratio of the flow cross section of the flattened portion 4a—about 0.19 mm$^2$—to that of each adjacent cylindrical portion (with an internal cross section of about 0.78 mm$^2$), this is slightly less than 25%.

Furthermore, the flattened portion 4a has a wall thickness e and a density d, the product e×d of which is approximately equal to 35.5 (with e=25 μm and d=1.42 g/cm$^3$), this being very much less than the values normally used, which are generally between 150 and 200 in the case of the microlines made of LDPE (which have a lower density than that of "Kapton", but a substantially greater thickness), in such a way that the attenuation by this portion 4a according to the invention of the particles to be counted, such as electrons or positrons, is considerably minimized.

As illustrated in FIG. 4a, the flattened portion 4a is equipped, facing its large faces and overhanging its small faces, with two sets of said detection diodes 6a capable of counting said particles in each liquid microsample flowing therein (this overhang of the diodes 6a makes it possible to optimize the "capture" of the particles to be counted).

The thermoforming process used to obtain this flattened portion 4a according to the invention comprises in particular the following steps:
  the portion 4a is placed, cold, in the forming mold;
  its two ends are connected to flexible microtubes for pressurization;
  pressure (1.5 bar of relative pressure) is applied;
  the mold is heated to 300° C. for 15 minutes;
  the mold is cooled under pressure; and
  the pressure is slowly lowered after cooling.

Figure 5:
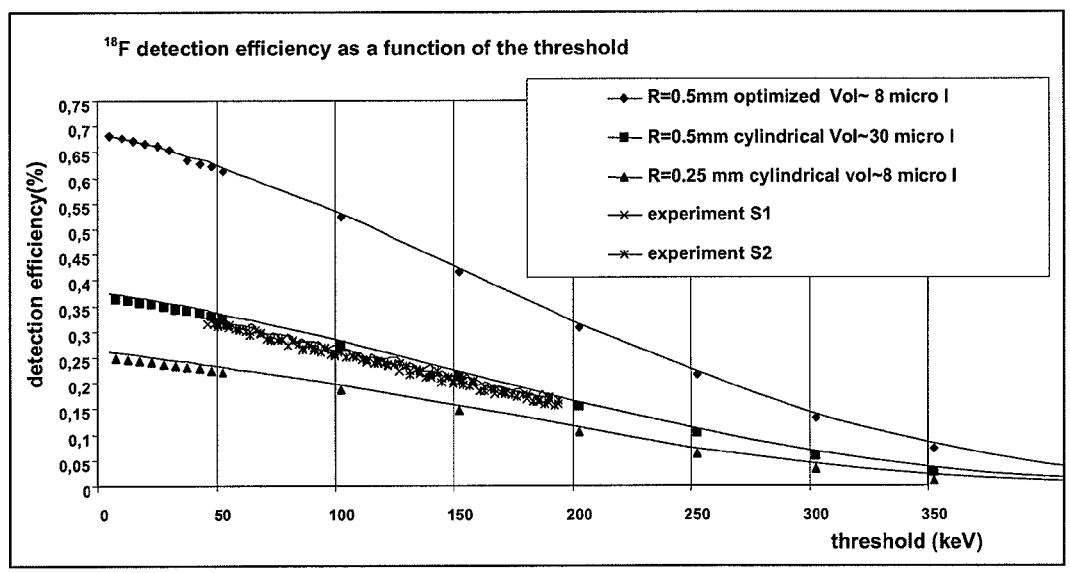
FIG. 5 is a graph illustrating the $^{18}$F radiotracer detection efficiency as a function of the detection threshold, for three types of sampling lines that include this flattened measurement portion according to the invention and, for comparative trials, two cylindrical microtubes.

The graph of FIG. 5 illustrates, in the form of simulation curves confirmed by experiment, the counting efficiency results obtained for two series of experiments S1 and S2, each carried out:
  with a line according to the invention of 0.5 mm radius for the cylindrical portions and incorporating this flattened portion 4a, with an 8 μl blood microsample volume taken (compatible with a mouse);
  with a first "control" line cylindrical over its entire length (i.e. with no flattened portion) having a radius of 0.5 mm and with a 30 μl blood microsample volume taken (compatible with a rat); and
  with a second "control" line cylindrical over its entire length (i.e. with no flattened portion) having a radius of 0.25 mm, with an 8 μl blood microsample volume taken.

Thanks to this flattened portion 4a, it may be noted that the positron detection efficiency increases, going from 32% with the cylindrical microtubes to more than 60% with the microtube of the invention, for the minimum threshold (approximately 46 keV). The gain is even greater as a cylindrical microtube line compatible with an 8 μl sample would give an efficiency of about 25%. The optimized microtube according to the invention thus makes it possible to work with 8 μl specimens, achieving more than 60% efficiency at the minimum threshold, compared with only 25% with a microtube entirely cylindrical over its length. This makes the sampling system 3 according to the invention particularly well suited for measuring the entry function of a mouse.

The system and the beta radiation counting method used in relation with the microtube 28 inserted into the connection device 20 of FIG. 3 and extended by the flattened portion 4a of the sampling line according to the invention illustrated in FIG. 4 will now be described in greater detail in relation to FIG. 1.

A few centimeters downstream of this connection device 20, each microsample passes as close as possible to the counter 6 for counting the particles resulting from the beta radioactivity, for which the wall thickness of the line causes only a very slight attenuation. The flattened portion 4a, fixed in the box 6b of the counter 6, makes it possible to minimize the amount of positron annihilation in the walls, and its geometry is such that it can contain the volume of a sample (either 30 μl or 8 μl) correctly centered beneath the six silicon detection diodes (measuring 10×10×0.3 mm$^3$) surrounding the portion 4a, as illustrated in FIG. 1. These diodes 6a are themselves surrounded by a lead shield 2 cm in thickness intended to eliminate the physical noise coming from the photons emanating from the animal 2. The rest of this measurement system 6 comprises an electronic processing/interfacing card, making the whole system compact and robust, being in the form of a box 6b of small dimensions (16×11×4 cm$^3$)

It is advantageous, in order to minimize the probability of annihilation in the blood of a positron coming from the beta radioactivity, to give the flexible microtube the flattened shape of the portion 4a, at least at the point where it passes in front of the diodes 6a. Moreover, as explained above, this geometric configuration also ensures that the liquid is spread out as a thin sheet, thereby increasing the area of liquid facing the detecting surfaces. The configuration adopted for the measurement system 6 is as follows.

The flattened portion 4a, with a wall thickness of 25 μm, is sandwiched between the diodes 6a, with a thickness of 0.3 mm (three diodes 6a at the top and three others at the bottom).

The read-out electronics for these diodes 6a and the electronics controlling the data acquisition and transfer have been integrated into a single electronic module, which has been optimized so as to reduce as far as possible the electronic noise, allowing the detection threshold to be minimized for optimum efficiency.

The "front-end" electronics (shaper and discriminator) is provided by an ASIC (comprising 16 channels, a common threshold, 16 outputs+1 OR). The threshold is adjusted by the user. The acquisition card is a configurable USB test card benefiting from the flexibility of the USB interface of personal computers and from the progress made in FPGA (Field Programmable Gate Array) configurable digital circuits. This allows a large number of signals to be rapidly processed and can be programmed from the interface of a computer.

The basic scheme is illustrated in FIG. 1. The catheter 21 coming from the artery of the animal 2 is extended by the microtube 28 of FIG. 3 arriving on one side of the box 6b, and then by the flattened portion 4a, which takes over inside the box 6b, the blood emerging on the other side of the latter. This blood flow is performed by the peristaltic pump 7. The volume of the microsamples taken can be adjusted, as can their sampling times. These parameters are controlled by the computer of the control device 9 of the installation 1.

The minimum time between two microsamplings is 1 second. To cover the dynamic range of the kinetics of the radiotracer in the blood, the microsamples are taken every second after the injection for about 30 seconds to 1 minute, and then they are taken in more spaced apart time intervals, the slope of the curve being more gentle during this phase.

As explained above with reference to FIG. 3, the connection between the sampling catheter 21 and the microtube 28 opening into the box 6*b* has been made so as to eliminate any dead volume that would cause two adjacent microsamples to be mixed. As regards the connections between the microtubes and the box 6*b*, these are designed to avoid any loss of volume of the microsamples. Furthermore, the dimensions of the two microtubes external to the box 6*b* are such that no diffusion between two adjacent microsamples is possible.

These blood microsamples are thus taken in discrete packets spatially and temporally and they thus progress without diffusion as far as the sample treatment system 8 where they are stored and advantageously subjected to the extraction of at least one of their phases or their components, for example subjected to a centrifugation.

It will be noted that this sampling system 3 according to the invention may advantageously be used in the field of preclinical research for the quantitative imaging of new tracers, especially in positron emission tomography (PET). In this case, the liquid in question is blood and the application consists in measuring the entry function for small animals, such as rats or mice. The small size of these animals, and therefore the small total amount of blood that they possess, limit the volume of each microsample to about 30 µl in the case of rats and about 8 µl in the case of mice.

The invention claimed is:

1. A fluid connection device which is useable for microsamples to be taken or to be injected and which is connected to a first line via a first opening in this device, which includes a second opening through which a second line passes, the second line communicating with the first line in order to transfer said microsamples, the device comprising:
said first and second lines;
a female fluid connector that defines said first opening and has an internal fitting surface terminating in a female radial end into which this first line opens; and
a male fluid connector that defines said second opening, which is fitted into the female connector via its external surface and terminates via its male radial end inside the female connector,
wherein this second line is formed from a flexible microtube which is pushed through the male connector axially beyond said male end, the free end of this second line pressing in a sealed manner against said female end so as to minimize a dead volume between the first line and the male connector.

2. The fluid connection device as claimed in claim 1, wherein said internal fitting surface of the female connector is a conical surface converging on said female end with the same conicity as said external surface of the male connector, which converges on said male end.

3. The fluid connection device as claimed in claim 2, wherein said male and female connectors are both connectors of the "Luer" type, as defined by the ISO 594-1 standard of 1986, or else of the "Luer-lock" type, as defined by the ISO 594-2 standard of 1998.

4. The fluid connection device as claimed in claim 3, wherein said second line extends beyond said male end by an axial length at least equal to the minimum distance (dl) separating said respective ends of the two connectors when the male connector is pushed into the connection position in the female connector in accordance with one or other of said standards.

5. The fluid connection device as claimed in claim 1, wherein said second line is provided, around its cylindrical wall and near its free end, with a stiffening means capable of stiffening it inside said female connector.

6. The fluid connection device as claimed in claim 5, wherein said stiffening means is formed from a ring made of a material that has a stiffness at least equal to that of said second line and is capable of being fastened thereto, this ring being mounted so as to bear between said second line and said conical internal fitting surface of said female connector.

7. The fluid connection device as claimed in claim 1, wherein said first line a flexible microtube suitable for taking said liquid from an animal or injecting it thereinto.

8. The fluid connection device as claimed in claim 6, wherein said stiffness of the ring is greater than that of said second line, said ring comprising a polymeric resin.

* * * * *